(12) United States Patent
Kim

(10) Patent No.: US 10,806,135 B2
(45) Date of Patent: Oct. 20, 2020

(54) FUMIGATION VAPORIZER

(71) Applicant: SAFEFUME Co., Ltd, Hoeneseone-gun, Gangwon-do (KR)

(72) Inventor: Hoe-geun Kim, Gangwon-do (KR)

(73) Assignee: SAFEFUME Co., Ltd (KR)

( * ) Notice: Subject to any disclaimer, the term of this patent is extended or adjusted under 35 U.S.C. 154(b) by 252 days.

(21) Appl. No.: 15/871,975

(22) Filed: Jan. 15, 2018

(65) Prior Publication Data

US 2018/0220639 A1    Aug. 9, 2018

(30) Foreign Application Priority Data

Feb. 3, 2017  (KR) .................. 10-2017-0015763

(51) Int. Cl.
*A01M 13/00* (2006.01)
*A01N 25/18* (2006.01)
(Continued)

(52) U.S. Cl.
CPC .......... *A01M 13/00* (2013.01); *A01M 21/043* (2013.01); *A61L 2/20* (2013.01);
(Continued)

(58) Field of Classification Search
CPC ..... A01M 13/00; A01M 21/043; A01N 25/18; A01N 29/02; B05B 7/0012; B05B 7/1686;
(Continued)

(56) References Cited

U.S. PATENT DOCUMENTS 3,548,151 A * 12/1970 Jung ................... A01M 13/00
                                                    392/396
5,825,975 A * 10/1998 Privas .................. B05B 7/1686
                                                    392/404
(Continued)

FOREIGN PATENT DOCUMENTS

EP          2681993 A1 *  8/2014  ............ A01M 13/00
KR       19940000852 B1     2/1994
(Continued)

*Primary Examiner* — Minh Chau T Pham
(74) *Attorney, Agent, or Firm* — Renaissance IP Law Group LLP

(57) ABSTRACT

Disclosed is a fumigation vaporizer capable of quickly vaporizing a fumigant, which is widely used in agriculture or quarantine to control insects or weeds, thereby safely and effectively carrying out fumigation, as compared to a conventional process. The fumigation vaporizer includes a housing, a fumigant supply pipe, a heater, a non-explosive gas supply member, a gas supply pipe, a vessel-type heater, a gas discharge pipe, and a controller. The housing is provided with a heating hollow portion at the lower portion of the inner cavity, in which the non-explosive gas heated and supplied by the vessel-type heater heats a bottom surface of the inner cavity while passing through the heating hollow portion. A bottom surface of the heating hollow portion is provided with an inlet port through which the non-explosive gas passes, and a top surface of the heating hollow portion opposite to the inlet portion is provided with an outlet port through which the non-explosive gas passing the heating hollow portion is supplied to the gas discharge pipe installed to the inner cavity.

13 Claims, 7 Drawing Sheets

(51) Int. Cl.
*A01N 29/02* (2006.01)
*B05B 12/02* (2006.01)
*B05B 12/10* (2006.01)
*B05B 1/20* (2006.01)
*B05B 7/16* (2006.01)
*A61L 2/20* (2006.01)
*A01M 21/04* (2006.01)
*B05B 7/00* (2006.01)
*B05B 1/00* (2006.01)

(52) U.S. Cl.
CPC ............ *B05B 7/0012* (2013.01); *B05B 7/164* (2013.01); *B05B 7/1686* (2013.01); *B05B 12/02* (2013.01); *B05B 12/10* (2013.01); *A61L 2202/11* (2013.01); *A61L 2202/14* (2013.01); *B05B 1/005* (2013.01); *B05B 1/20* (2013.01)

(58) Field of Classification Search
CPC ......... B05B 12/02; B05B 12/10; B05B 7/164; B05B 1/005; B05B 1/20; B05B 7/16; A61L 2/20; A61L 2202/11; A61L 2202/14
USPC ..... 422/32, 129, 34, 302; 47/1.44, 1.7, 48.5; 43/144; 111/118, 120; 392/386, 404; 222/146.1–146.5, 644, 646
See application file for complete search history.

(56) References Cited

U.S. PATENT DOCUMENTS

| | | | |
|---|---|---|---|
| 6,505,437 B1* | 1/2003 | Johnstone | A01M 21/04 47/1.44 |
| 2005/0232810 A1* | 10/2005 | Yamamoto | A01M 13/00 422/34 |
| 2011/0044852 A1* | 2/2011 | Ryan | A01M 13/00 422/32 |
| 2014/0112827 A1* | 4/2014 | Fernandez | A01N 25/18 422/28 |

FOREIGN PATENT DOCUMENTS

| | | |
|---|---|---|
| KR | 200304896 | 2/2003 |
| KR | 100382684 B1 | 7/2003 |
| KR | 100523676 B1 | 12/2005 |
| KR | 100742635 B1 | 7/2007 |
| KR | 20140011880 A | 1/2014 |
| KR | 101564458 B1 | 11/2015 |

\* cited by examiner

FUMIGATION VAPORIZER

CROSS REFERENCE TO RELATED APPLICATION

This U.S. non-provisional patent application claims priority under 35 U.S.C. § 119 to Korean Patent Application No. 10-2017-0015763 filed in the Korean Intellectual Property Office on Feb. 3, 2018, the entire contents of which are incorporated herein by reference.

BACKGROUND

1. Technical Field

The present disclosure relates to a fumigation apparatus, and, more particularly, to a fumigation vaporizer capable of quickly vaporizing a fumigant, which is widely used in agriculture or quarantine to control insects or weeds, thereby safely and effectively carrying out fumigation, as compared to a conventional method.

2. Background of the Related Art

A fumigant means any volatile chemical compound used as a disinfectant or pesticide.

In general, the fumigant is widely used in agriculture or quarantine due to its insecticidal, sterilizing and weeding effects.

Such a fumigant includes hydrogen cyanide, calcium cyanide, carbon dioxide, sulfurous acid gas, chloropicrin, carbon tetrachloride, ethylene dichloride, ethylene dibromide, p-dichlorobenzene, and γ-benzene hexachloride (BHC), and is used to insecticide and sterilize warehouses, vessels, fruits, or soil.

If much fumigant is remained in the soil, the soil is polluted. If the warehouse or vessel is washed out by washing water after sterilization, the water is polluted by the fumigant contained in the washing water. Therefore, the fumigant is restricted in use.

The fumigant is generally used in a liquid type which is heated to produce a volatile fumigated substance, and then the volatile fumigated substance is supplied to a subject to be fumigated, for example, warehouse, vessels, fruits or soil.

It is widely known in those skilled in the art that the current method uses methyl bromide as the fumigant.

In the case of the methyl bromide which is known as an ozone-depleting chemical, the volatile fumigated substance is generally supplied through a simple vaporizer in order to avoid cold treatment or reduce damage to the subjects to be fumigated. There is a problem in that a worker can breathe in the volatile fumigated substance which is left in a hose after it is supplied.

In case of a fumigant (pressurized gas mixed with EF and $CO_2$) which is newly developed as a substitute of methyl bromide, a vaporizer is used due to a freezing phenomenon of a gas tube in use. A tank is filled with the expensive mixed gas at high pressure, and a worker is in danger due to the heavy tank. Therefore, a new fumigation vaporizer should be developed in view of the above circumstances.

SUMMARY

Therefore, the present disclosure has been made in view of the above problems, and an object of the present disclosure is to provide a fumigation vaporizer capable of quickly vaporizing a fumigant, which is widely used in agriculture or quarantine to control insects or weeds, thereby safely and effectively carrying out fumigation, as compared to a conventional method.

Another object of the present disclosure is to provide a fumigation vaporizer capable of improving performance of vaporizing a fumigant by heating a bottom surface of an inner cavity of a housing, vaporizing the fumigant which is left on the bottom surface of the inner cavity if the fumigant is vaporized and thus its level goes down, to decrease all expenses caused by the use of the fumigant, and simplifying the structure of the fumigation vaporizer.

In order to achieve the above objects, there is provided a fumigation vaporizer including: a housing including an inner cavity, and provided at an upper portion with an inlet port to supply a fumigant to the inner cavity and an outlet port to discharge a volatile fumigated substance from the inner cavity; a fumigant supply pipe configured to supply the fumigant to the inner cavity of the housing, one end of the fumigant supply pipe extending to the inner cavity through the inlet port, and the other end being connected to a fumigant reservoir; a heater configured to heat a lower portion of the housing, thereby producing the volatile fumigated substance by heating the fumigant supplied through the fumigant supply pipe; a non-explosive gas supply member provided to an outside of the housing to supply the non-explosive gas; a gas supply pipe having one end connected to the non-explosive gas supply member and the other end connected to the housing to supply the non-explosive gas to the inner cavity from the non-explosive gas supply member; a vessel-type heater installed to a portion of the gas supply pipe to heat the non-explosive gas supplied to the housing; a gas discharge pipe provided with a plurality of nozzle holes to spray the non-explosive gas supplied from a non-explosive gas tank, thereby supplying the non-explosive gas which is heated by the vessel-type heater to a lower portion of the housing, thereby upwardly moving the volatile fumigated substance; and a controller to control operation of the heater, the housing being provided with a heating hollow portion at the lower portion of the inner cavity, in which the non-explosive gas heated and supplied by the vessel-type heater heats a bottom surface of the inner cavity while passing through the heating hollow portion, and a bottom surface of the heating hollow portion being provided with an inlet port through which the non-explosive gas passes, and a top surface of the heating hollow portion opposite to the inlet portion being provided with an outlet port through which the non-explosive gas passing the heating hollow portion is supplied to the gas discharge pipe installed to the inner cavity.

The gas discharge pipe is a coil-type gas discharge pipe which is installed in a shape of a coil to the lower portion of the inner cavity, and a guide protrusion protrudes upwardly from a center portion of the coil-shaped gas discharge pipe so that the fumigant does not collect around a center portion of the gas discharge pipe, if a level of the fumigant goes down due to the volatile fumigated substance to be produced from the fumigant supplied to the inner cavity.

The guide protrusion is formed in any one of a hemispherical shape and a conic shape which protrudes upwardly from the center portion of the coil-shaped gas discharge pipe.

The non-explosive gas supply member includes a non-explosive gas tank which is filled with the non-explosive gas therein.

The non-explosive gas supply member includes a nitrogen generator to continuously generate and supply a nitrogen gas, the nitrogen generator has a compressor configured to pressurize air sucked from the atmosphere and then supply the pressurized air to the nitrogen generator; a first nitrogen separating tank supplied by the pressurized air from the compressor to separate nitrogen; a second nitrogen separating tank supplied by the pressurized air from the compressor to separate nitrogen; an absorbent respectively disposed in the first nitrogen separating tank and the second nitrogen separating tank to absorb oxygen contained in the air; a nitrogen reservoir alternatively supplied by the nitrogen from the first nitrogen separating tank and the second nitrogen separating tank, and supplying the nitrogen to the housing through the gas supply pipe; and a controller to control concentration of the oxygen supplied to the first nitrogen separating tank and the second nitrogen separating tank so that the level is maintained at a level of 100 ppm, and the controller has an automatic time switch to variably produce a yield of the nitrogen from the nitrogen generator depending upon amounts of nitrogen to be used by the housing, and the automatic time switch variably controls a supply time of the pressurized air to be selectively supplied to the first nitrogen separating tank and the second nitrogen separating tank to produce the nitrogen, while the concentration of oxygen to be respectively supplied to the first nitrogen separating tank and the second nitrogen separating tank is maintained at the level of 100 ppm.

The heater is installed to enclose an outer peripheral surface of the housing which corresponds to the lower portion of the housing.

The nozzle hole has a decreased-diameter hole which is formed in such a way that a diameter is gradually decreased toward a spray direction of the non-explosive gas, an orifice extended hole which communicates with the decreased-diameter hole, and is formed by an extended portion of a minimal diameter of the decreased-diameter hole, and an increased-diameter hole which communicates with the orifice extended hole, of which a diameter is gradually increased toward the spraying direction of the non-explosive gas.

The vessel-type heater is provided with a hot wire to heat the non-explosive gas, and the hot wire is arranged in any one of a zigzag shape, a U-shape and a spiral shape to promote heating.

The non-explosive gas is any one selected from a group consisting of nitrogen ($N_2$), carbon dioxide ($CO_2$), and helium (He). The fumigant is any one selected from a group consisting of methyl bromide, ethyl formate, methyl formate, liquefied fumigation substance (e.g., MITC, AITC or monoterpenes) mixable with ethyl formate, methyl isothicyante (MITC), allyl isothiocyanate (AITC), aluminum phosphide, magnesium phosphide, phosphine, sulfuryl floride, methyl iodide, cyanogen, metham sodium, carbonyl sulfide, carbon tetrachloride, and dimethyl disulfide. The housing and the outlet port are provided with a pressure gauge, respectively. The housing is provided with a level gauge at one side thereof.

With the above configuration, the fumigation vaporizer can quickly vaporizing the fumigant, which is widely used in agriculture or quarantine to control insects or weeds, thereby safely and effectively carrying out fumigation, as compared to the conventional method.

In addition, the fumigation vaporizer can improve performance of vaporizing the fumigant by heating the bottom surface of the inner cavity of the housing, vaporizing the fumigant which is left on the bottom surface of the inner cavity if the fumigant is vaporized and thus its level goes down, to decrease all expenses caused by the use of the fumigant, and simplifying the structure of the fumigation vaporizer.

DETAILED DESCRIPTION OF THE PREFERRED EMBODIMENT

Preferred embodiments of the present disclosure will now be described in detail with reference to the accompanying drawings.

The embodiment of the present disclosure is intended to be illustrative only. Numerous alternative embodiments may be devised by those skilled in the art without departing from the scope of the following claims.

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the inventive ad defined by the appended claims and equivalents thereof.

Figure 1:
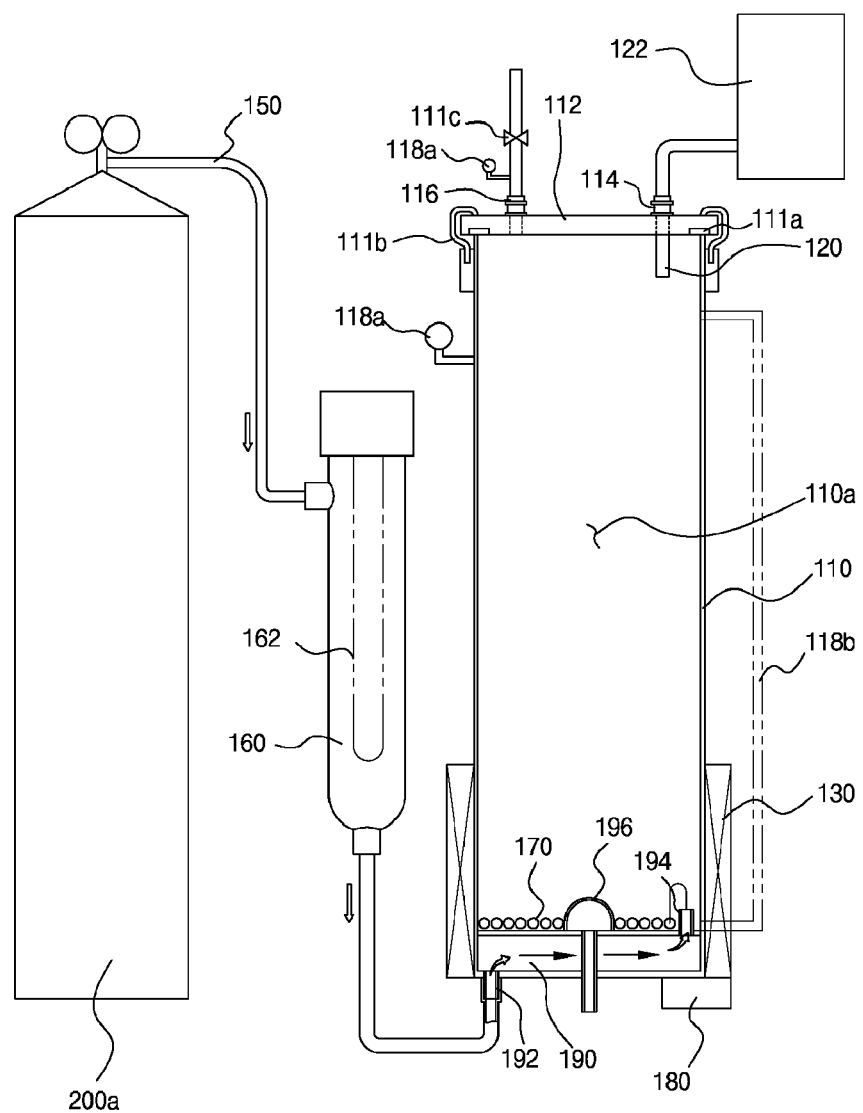
FIG. 1 is a view schematically illustrating the structure of a fumigation vaporizer according to one embodiment of the present disclosure.
Figure 2:
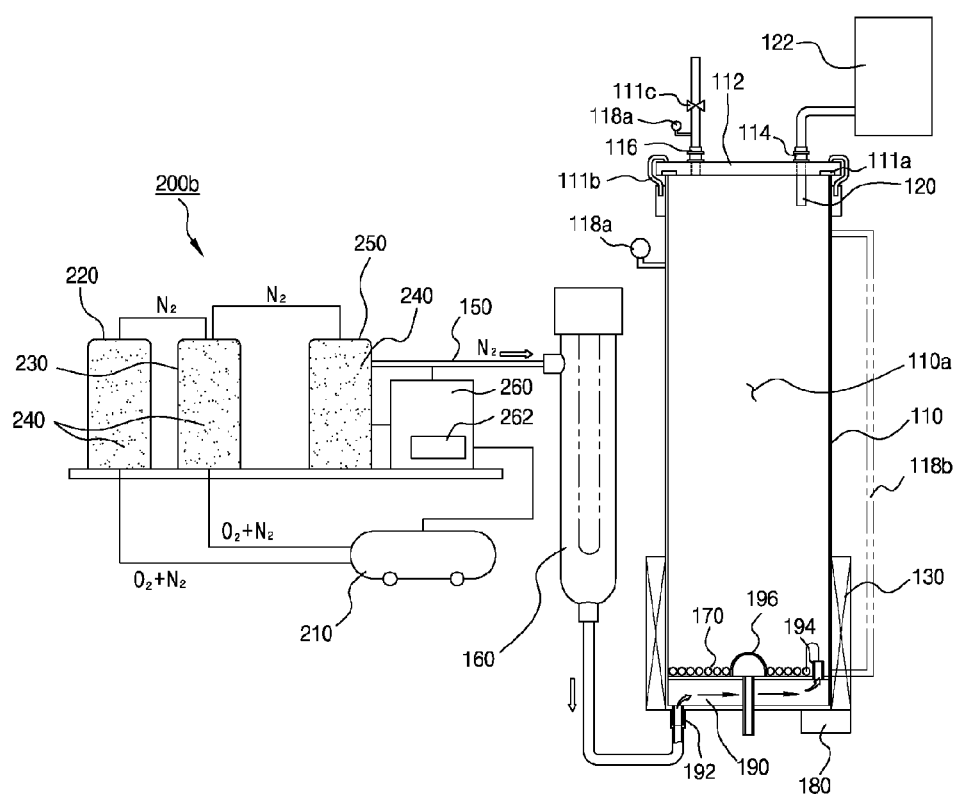
FIG. 2 is a view schematically illustrating the structure of the fumigation vaporizer according to one embodiment of the present disclosure.
Figure 3:
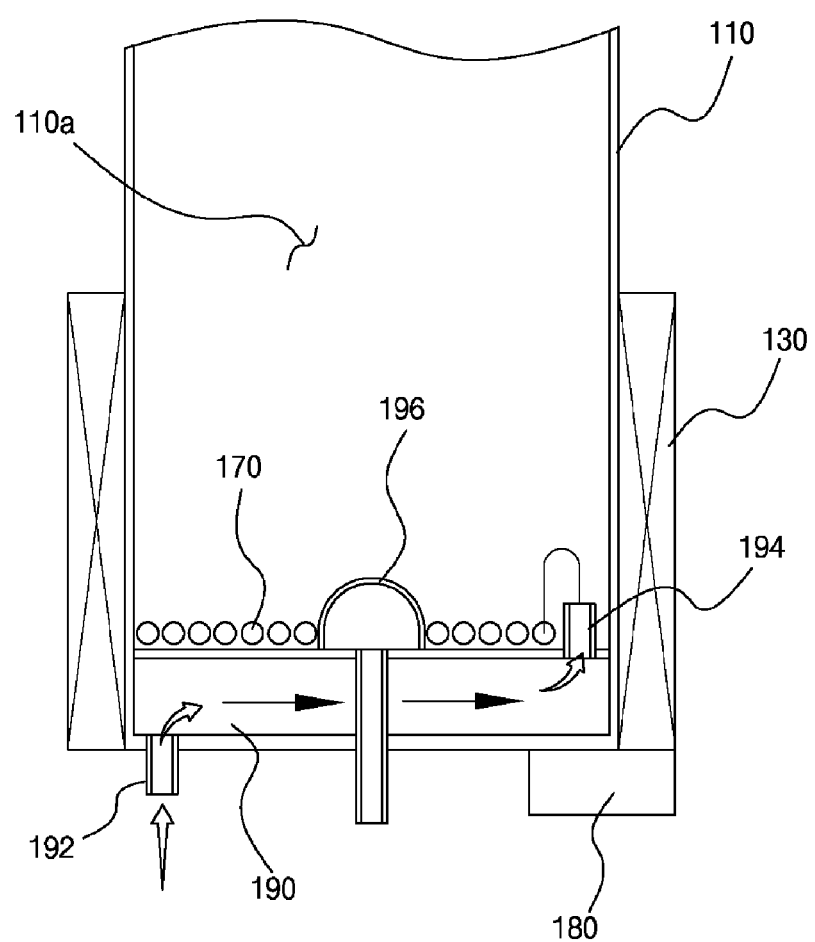
FIG. 3 is an enlarged view of a major part in the fumigation vaporizer according to one embodiment of the present disclosure.
Figure 4:
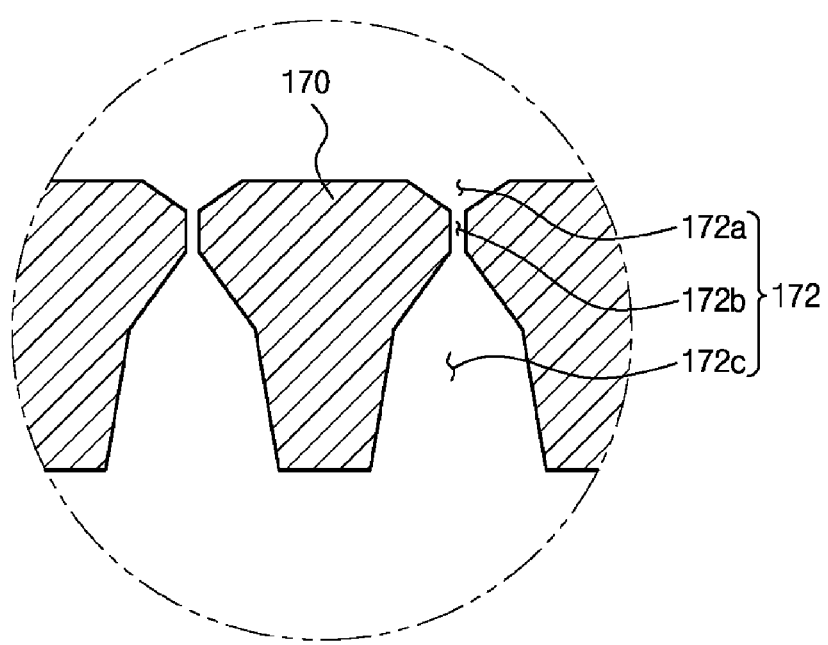
FIG. 4 is a view of nozzle holes formed in a gas discharge pipe of the fumigation vaporizer according to one embodiment of the present disclosure.
Figure 5:
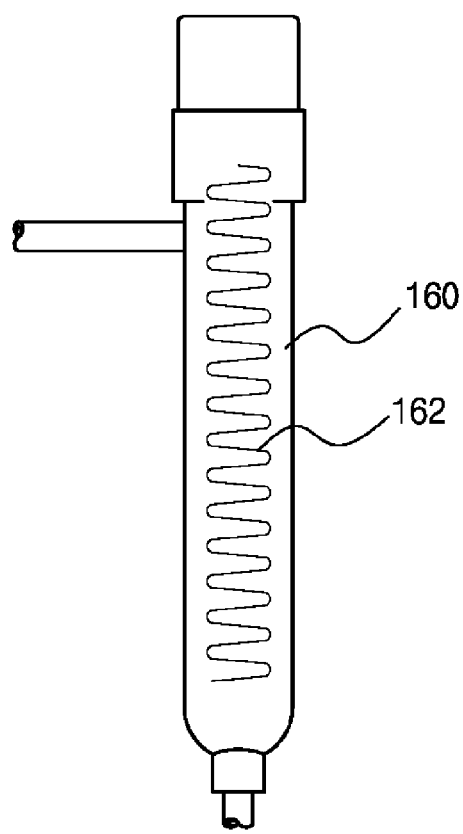
FIGS. 5 and 6 are views illustrating some examples of a vessel-type heater of the fumigation vaporizer according to one embodiment of the present disclosure.
Figure 6:
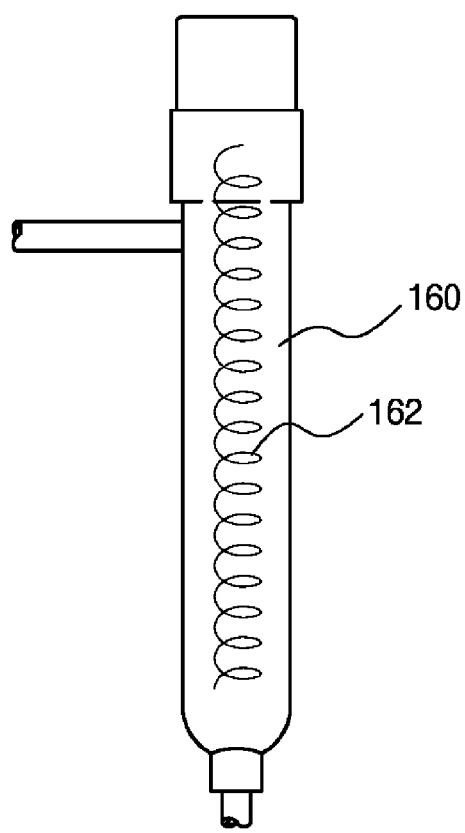
Figure 7:
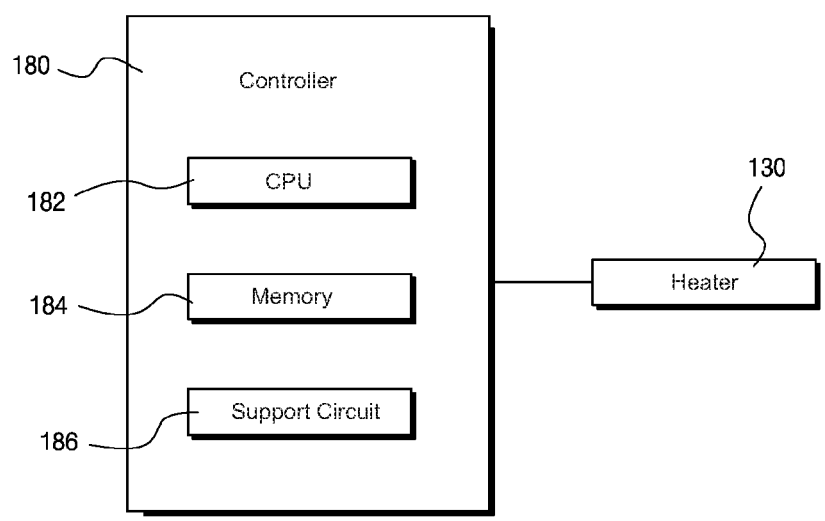
FIG. 7 is a control block diagram of the fumigation vaporizer according to one embodiment of the present disclosure.

FIG. 1 is a view schematically illustrating the structure of a fumigation vaporizer according to one embodiment of the present disclosure. FIG. 2 is a view schematically illustrating the structure of the fumigation vaporizer according to one embodiment of the present disclosure. FIG. 3 is an enlarged view of a major part in the fumigation vaporizer according to one embodiment of the present disclosure. FIG. 4 is a view of nozzle holes formed in a gas discharge pipe of the fumigation vaporizer according to one embodiment of the present disclosure. FIGS. 5 and 6 are views illustrating some examples of a vessel-type heater of the fumigation vaporizer according to one embodiment of the present disclosure. FIG. 7 is a control block diagram of the fumigation vaporizer according to one embodiment of the present disclosure.

As illustrated in the drawings, the present disclosure relates to a fumigation vaporizer capable of quickly vaporizing a fumigant, which is widely used in agriculture or quarantine to control insects or weeds, thereby safely and effectively carrying out fumigation, as compared to a conventional process, and the fumigation vaporizer includes a housing 110, a fumigant supply pipe 120, a heater 130, a non-explosive gas supply member, a gas supply pipe 150, a vessel-type heater 160, a gas discharge pipe 170, and a controller 180.

The housing 110 is a cylindrical structure, and an inner cavity 110a is formed to which a fumigant is supplied.

The housing 110 is provided with a lid 112 which is detachably installed to an upper opening thereof. The maintaining and cleaning work can be performed in the housing 110 in the state in which the lid 112 is opened.

The lid 112 installed to the housing 110 is provided with a packing 111a to maintain a sealing force between the lid 112 and the housing 110, and the lid 112 can be engaged to the housing 110 by a coupler 111b.

The lid 112 may be provided with at one side an inlet port 114 to supply the fumigant to the housing, and at the other side an outlet port 116 to discharge a volatile fumigated substance.

The housing 110 is provided with a fumigant supply pipe 120 to supply the fumigant to the inner cavity 110a.

One end of the fumigant supply pipe 120 extends to the inner cavity 110a through the inlet port 114 provided to the lid 112, and the other end is connected to a fumigant reservoir 122, so that the fumigant is supplied to the inner cavity through the fumigant supply pipe.

The outlet port 116 provided to the lid 112 which is coupled to the housing 110 acts to discharge the volatile fumigated substance from the housing. Although now shown in the drawings, the outlet port 116 for discharging the volatile fumigated substance may be further provided with an anti-liquefying heater to prevent the volatile fumigated substance from liquefying.

The housing 110 and the outlet port 116 are provided with a pressure gauge 118a, respectively, and the outlet port 116 for discharging the volatile fumigated substance is provided with a valve 111c.

The housing 110 may be provided with a level gauge 118b at one side thereof. The level gauge 118b is made of a pipe which is connected to the inside of the housing, so that a user can easily check amounts of the fumigant in the housing 110.

The fumigant supplied to the inner cavity of the housing 110 is heated by the heater 130 to produce the volatile fumigated substance.

In this embodiment, the fumigant can be any one selected from a group consisting of methyl bromide, ethyl formate, methyl formate, liquefied fumigation substance (e.g., MITC, AITC or monoterpenes) mixable with ethyl formate, methyl isothicyante (MITC), allyl isothiocyanate (AITC), aluminum phosphide, magnesium phosphide, phosphine, sulfuryl floride, methyl iodide, cyanogen, metham sodium, carbonyl sulfide, carbon tetrachloride, and dimethyl disulfide.

The liquefied fumigation substance mixable with ethyl formate may include mono and sesquiterperinoids, such as methyl isothiocynante, ally istothiocyanate, ally anisole, methyl benzoate, camphor, carvone, 1,8-cineole, p-cymene, eugenol, limonene, menthone, alpha pinene, and beta pinene.

Natural essential oil may include natural substances having insecticidal and sterilizing effects, such as lavender, lemon, lime, peppermint, pine, rosemary, thyme, or tea tree oil.

The non-explosive gas supply member may be provided to the outside of the housing 110, as illustrated in FIG. 1, and includes a non-explosive gas tank 200a filled with a non-explosive gas therein.

In this embodiment, the non-explosive gas may be any one selected from a group consisting of nitrogen ($N_2$), carbon dioxide ($CO_2$), and helium (He).

The non-explosive gas supply member may be provided to the outside of the housing 110, as illustrated in FIG. 2, and includes a nitrogen generator 200b.

The nitrogen generator 200b is configured to extract nitrogen from the atmosphere, and has an automatic time switch 262 to operate a compressor 210 depending upon the amounts of nitrogen to be used by the housing 110. The nitrogen generator 200b can variably control a time of pressurized air to be selectively supplied to a first nitrogen separating tank 220 and a second nitrogen separating tank 230, while concentration of oxygen to be respectively supplied to the first nitrogen separating tank 220 and the second nitrogen separating tank 230 is maintained at a level of 100 ppm by the automatic time switch 262.

Accordingly, the nitrogen generator is controlled by the automatic time switch 262 which operates the compressor according to the supply time of the pressurized air to be selectively supplied to the nitrogen separating tanks.

Referring to the drawings, the nitrogen generator 200b preferably includes the compressor 210, the first nitrogen separating tank 220, the second nitrogen separating tank 230, an absorbent 240, a nitrogen reservoir 250, a controller 260, and the automatic time switch 262.

The compressor 210 is configured to pressurize the air and then supply the pressurized air sucked from the atmosphere to the nitrogen generator.

The first nitrogen separating tank 220 and the second nitrogen separating tank 230 are connected to each other by a supply pipe through which the air pressurized by the compressor 210 is supplied to the nitrogen generator.

The first nitrogen separating tank 220 separates the nitrogen from the pressurized air supplied by the compressor 210.

The second nitrogen separating tank 230 separates the nitrogen from the pressurized air supplied by the compressor 210.

The absorbent 240 is respectively disposed in the first nitrogen separating tank 220 and the second nitrogen separating tank 230 to absorb the oxygen contained in the air.

The absorbent 240 absorbs the oxygen, and the nitrogen passes through the absorbent.

The nitrogen passing through the first nitrogen separating tank 220 and the second nitrogen separating tank 230 is supplied to the nitrogen reservoir 250.

The nitrogen passing through the first nitrogen separating tank 220 is supplied to the second nitrogen separating tank 230, and then the nitrogen discharged from the second nitrogen separating tank 230 is supplied to the nitrogen reservoir 250.

If the absorbent 240 is disposed in the nitrogen reservoir 250, the absorbent absorbs the oxygen contained in the nitrogen to supply high-purity nitrogen.

The nitrogen reservoir 250 is connected to the housing 110, and thus the nitrogen is supplied to the housing 110.

In this instance, the nitrogen reservoir 250 is connected to the housing 110 by the gas supply pipe 150, and the gas supply pipe 150 supplies the nitrogen discharged from the nitrogen storage 250 to the housing 110.

The nitrogen reservoir 250 and the nitrogen generator 200b may be controlled by the controller 260.

The controller 260 controls the nitrogen reservoir 250 and the nitrogen generator 200b so that the concentration of oxygen to be supplied to the first nitrogen separating tank 220 and the second nitrogen separating tank 230 is maintained at the level of 100 ppm.

The controller 260 can vary the concentration of oxygen, and also can maintain the concentration of oxygen at a constant level.

Also, the controller 260 can determine whether or not the compressor 210 operates normally, thereby adjusting amounts of nitrogen and the concentration of oxygen.

Preferably, the automatic time switch 262 is controlled by the controller 260.

The automatic time switch 262 can maintain the concentration of oxygen to be supplied to the first nitrogen separating tank 220 and the second nitrogen separating tank 230 at the level of 100 ppm constantly, and can control the supply time of the pressurized air to be selectively supplied by the compressor 210.

Specifically, the automatic time switch 262 sets the concentration of oxygen by the level of 100 ppm, and if the switching time of the first nitrogen tank 220 and the second nitrogen tank 230 is extended, the pressurized air supplied from the compressor 210 is decreased.

The automatic time switch 262 can variably produce the amounts of the nitrogen from the nitrogen generator depending upon variations in the nitrogen used in the housing 110.

For example, comparing a common nitrogen generator and the nitrogen generator used for the fumigation vaporizer according to the present disclosure, the common nitrogen generator requires 10 liters of pressurized air when producing 10 liters of nitrogen. However, the common nitrogen generator also requires 10 liters of pressurized air when producing 1 liter of nitrogen.

The nitrogen generator according to the present disclosure supplies 10 liters of pressurized air from the compressor 210 when producing 10 liters of nitrogen.

Also, the nitrogen generator according to the present disclosure requires 1 liter of pressurized air from the compressor 210 when producing 1 liter of nitrogen.

TABLE 1

| Common nitrogen generator | | | Inventive nitrogen generator | | |
|---|---|---|---|---|---|
| Pressurized air l/h | Nitrogen l/h | O$_2$ ppm | Pressurized air l/h | Nitrogen l/h | O$_2$ ppm |
| 64,212 | 12,000 | 100 | 64,212 | 12,000 | 100 |
| 63,182 | 11,000 | 80 | 53,133 | 11,000 | 100 |
| 62,358 | 10,000 | 50 | 47,272 | 10,000 | 100 |
| 60,576 | 9,000 | 30 | 42,343 | 9,000 | 100 |

Consumers do not require a low level in concentration of oxygen.

As can be noted from Table 1 above, if the concentration of oxygen is set by the level of 100 ppm, the present disclosure can save 30% of total pressurized air, as compared to the common nitrogen generator, when producing the nitrogen of the same amounts.

Specifically, the common nitrogen generator should continuously operate the compressor to increase a yield of nitrogen, if the level of oxygen goes down in the state in which the level of oxygen is not set.

According to the nitrogen generator according to the present disclosure, if the level of oxygen is set by the level of 100 ppm, the pressure of the pressurized air goes down even though the yield of nitrogen is equal to that of the common nitrogen generator. It is possible to produce the same amounts of nitrogen as the common nitrogen generator even at the low pressure.

Therefore, it is not necessary to continuously operate the compressor 210.

If the level of oxygen goes down below the level of 100 ppm, the time of the pressurized air to be selectively supplied to the first nitrogen separating tank 220 and the second nitrogen separating tank 230 by the compressor 210 is extended.

Specifically, the automatic time switch 262 adjusts the time of oxygen to be selectively supplied to the first nitrogen separating tank 220 and the second nitrogen separating tank 230 to vary the amounts of the pressurized air to be supplied according to the amounts of nitrogen used in the housing 110.

The automatic time switch 262 can control the compressor 210 which selectively supplies the pressurized air to the first nitrogen separating tank 220 and the second nitrogen separating tank 230, thereby varying the amounts of the pressurized air to be supplied to the compressor.

The automatic time switch 262 maintains the level of oxygen by 100 ppm. If the level of oxygen goes down below 100 ppm, the automatic time switch operates the compressor 210 in the unit of shift time. If the level of oxygen is maintained at 100 ppm, the automatic time switch automatically shuts off the compressor to stop the operation of the compressor 210.

Also, automatic time switch 262 stops the operation of the compressor 210 according to the shift time of the pressurized air to be supplied, thereby decreasing power consumption of the compressor 210.

The present disclosure can continuously produce and supply the nitrogen to the housing 110, thereby improving the yield.

The housing 110 is provided with the vessel-type heater 160 to preheat the non-explosive gas, i.e., nitrogen gas, when the nitrogen gas is supplied to the lower portion of the housing 110.

The vessel-type heater 160 is provided to the gas supply pipe, one end of the gas supply pipe being connected to the non-explosive gas supply member to supply the non-explosive gas to the inner cavity 110a of the housing 110 from the non-explosive gas supply member.

Also, the vessel-type heater 160 for heating the non-explosive gas which is fed to the vessel-type heater and then discharging the heated gas from the vessel-type heater is equipped with a hot wire 162 for heat-exchanging with the non-explosive gas.

The hot wire 162 may be arranged in any one of a zigzag shape, a U-shape and a spiral shape to promote the heating.

Since the vessel-type heater 160 is provided to the housing, the nitrogen gas to be supplied is heated, thereby solving a reduced effect problem due to cold nitrogen gas.

The non-explosive gas which is heated by the vessel-type heater 160 and then is supplied to the lower portion of the housing 110 is sprayed, and, to the end, the inside of the housing 110 is provided with the gas discharge pipe 170.

The gas discharge pipe 170 supplies the non-explosive gas which is heated by the vessel-type heater 160, to the lower portion of the housing 110, thereby upwardly moving a volatile fumigated substance which is vaporized by the heater 130.

The gas discharge pipe 170 is preferably disposed in a coil pattern in the inner lower end of the housing 110. Specifically, the gas discharge pipe 170 may be a coil-type gas discharge pipe which is installed in the shape of a coil to the lower portion of the housing 110a.

A guide protrusion 196 protrudes from a center portion of the coil-shaped gas discharge pipe so that the fumigant does not collect around the center portion of the gas discharge pipe, if the level of the fumigant goes down due to the volatile fumigated substance to be produced from the fumigant supplied to the inner cavity 110a. Therefore, the guide protrusion 196 is preferably formed in such a way that it protrudes upwardly from the center portion of the coil-shaped gas discharge pipe, which is one of characteristic elements of the present disclosure.

In this instance, the guide protrusion 196 may be formed in any one of a hemispherical shape and a conic shape which protrudes upwardly from the center portion of the coil-shaped gas discharge pipe.

For example, if the gas discharge pipe 170 is formed in the shape of the coil, there is an empty space in the center portion of the coil. Since the fumigant is left in the empty space when the level of the fumigant goes down, it is not possible to completely vaporize the fumigant.

In order to solve the above problem, the guide protrusion 196 protrudes upwardly from the empty space, so that the fumigant is collected around the guide protrusion 196 to completely vaporize the fumigant.

The gas discharge pipe 170 is preferably provided with a plurality of nozzle holes 172. The gas supply pipe 150 and the gas discharge pipe 170 may be made from stainless steel to prevent corrosion, and the gas discharge pipe 170 is provided with the plurality of nozzle holes 172 through which the non-explosive gas supplied from the non-explosive gas supply member is sprayed.

The nozzle hole 172 may have 10 to 30 mm in diameter. Of course, the present disclosure is not limited thereto.

One examples of the nozzle holes 172 is illustrated in FIG. 4, the nozzle hole consisting of a decreased-diameter hole 172a, an orifice extended hole 172b, and an increased-diameter hole 172c.

The decreased-diameter hole 172a is formed in such a way that a diameter is gradually decreased toward a spray direction of the non-explosive gas. The decreased-diameter hole 172a is designed to prevent vortex of the volatile fumigated substance when it first flows through the nozzle hole 172, so that the volatile fumigated substance can flow evenly and stably.

The orifice extended hole 172b communicates with the decreased-diameter hole 172a, and is formed by an extended portion of the minimal diameter of the decreased-diameter hole 172a. It is possible to adjust flow velocity of the volatile fumigated substance by changing the shape of the orifice extended hole 172b.

The increased-diameter hole 172c communicates with the orifice extended hole 172b, and a diameter thereof is gradually increased toward the spraying direction of the non-explosive gas. The increased-diameter hole 172c is designed to evenly and stably spray the volatile fumigated substance.

Even though the nozzle hole 172 is not a simple hole, but is configured to have the decreased-diameter hole 172a, the orifice extended hole 172b, and the increased-diameter hole 172c, the nozzle hole 172 can use the fumigant which is widely used for agriculture and quarantine inspection due to the insecticidal, disinfecting and weeding effect, in a safe and effective manner rather than a conventional manner.

Also, it is possible to reduce all expenses caused by the use of the fumigant, and to simplify the apparatus.

The lower portion of the housing 110 is provided with the heater 130 to heat the fumigant supplied and dropped and thus produce the volatile fumigated substance.

In this embodiment, the heater 130 is preferably installed to enclose an outer peripheral surface corresponding to the lower region of the housing 110.

As a result, the fumigation vaporizer according to this embodiment can supply the fumigant which is widely used for agriculture and quarantine inspection due to the insecticidal, disinfecting and weeding effect, to the housing, and produce the volatile fumigated substance by heating the fumigant, so that the substance quickly moves up with the nitrogen gas to be used as a fumigated state in a safe and effective manner.

Specifically, the present disclosure can use the fumigant in the safe and effective manner rather than the conventional manner, and can reduce all expenses caused by the fumigant, as well as the simplified apparatus.

According to the present disclosure, the housing 110 is preferably provided with a heating hollow portion 190 at the lower portion of the inner cavity 110a, and the non-explosive gas heated and supplied by the vessel-type heater 160 heats a bottom surface of the inner cavity 110a while passing through the heating hollow portion 190. The heating hollow portion 190 is the major characteristic element of the present disclosure.

The bottom surface of the heating hollow portion 190 is provided with an inlet port 192 through which the non-explosive gas passes, and a top surface of the heating hollow portion 190 opposite to the inlet portion 192 is provided with an outlet port 194 through which the non-explosive gas passing the heating hollow portion 190 is supplied to the gas discharge pipe 170 installed to the inner cavity 110a.

When the non-explosive gas heated and supplied by the vessel-type heater 160 passes the heating hollow portion 190 through the inlet port 192, the inner cavity 110a is heated. After that, the non-explosive gas is supplied to the gas discharge pipe 170 through the outlet port 194, thereby improving the performance.

The fumigation vaporizer further includes the controller 180 to control the operation of the heater 130. As illustrated in FIG. 7, the controller may include a CPU 182, a memory 184, and a support circuit 186.

The CPU 182 may be any one of commercially available computer processors to control the operation of the heater 130.

The memory 184 is connected to the CPU 182. The memory 184 may be installed at a remote position as a recordable medium which can be read by a computer. For example, the memory 184 is at least one of an RAM, ROM, a floppy disc, a hard disc and any digital storage which can be easily used.

The support circuit 186 is connected to the CPU 182 to support typical operations of the processor.

The support circuit 186 may include a cache, a power supply, a clock circuit, an input/output circuit, and a sub-system.

In this embodiment, the controller 180 controls the operation of the heater 130. In this instance, a process of the controller 180 to control the operation of the heater 130, and etc. may be stored in the memory 184. A software routine may be typically stored in the memory 184. The software routine may be stored in or executed by other central processing unit (not illustrated).

Although the present disclosure has been explained that the process is executed by the software routine, at least a part of the process can be executed by hardware. The processes of the present disclosure can be realized by a software which is executed by the computer system, can be realized by hardware, such as ICs, or can be realized by a combination of software and hardware.

The fumigation vaporizer according to the present disclosure can use the fumigant, which is widely used for agriculture and quarantine inspection due to the insecticidal, disinfecting and weeding effect, in the safe and effective manner rather than the conventional manner.

Also, the fumigation vaporizer according to the present disclosure can reduce all expenses caused by the use of the fumigant, and to simplify the apparatus.

The effects of the present disclosure will be now explained in detail. In view of the use of fumigation vaporizer, the present disclosure can reduce the use of methyl bromide which is ozone-depleting chemical, and promote economic use of expensive materials.

A biological control effect may be lowered in case where a penetrating depth of a gas itself is low upon fumigating imported fruits and vegetables, but the present disclosure can avoid cold treatment or decrease damage to the subjects to be fumigated by adding a function of the non-explosive gas, thereby maximizing the fumigation effect.

The effects of the present disclosure are summarized as follows:

In addition to the function of the simple fumigation vaporizer according to the related art which is using on spot, for example, the combination of the nitrogen gas and the fumigation vaporizer can be used, thereby improving the efficiency of the volatile fumigated substance and safely using the same. In particular, the nitrogen gas is supplied in an atomizing way through the nozzles, thereby maximizing the function.

Also, since vapor pressure is increased by the above reason, the penetrating force of the gas is increased to maximize the fumigation effect of the subject to be fumigated, for example, banana, orange, or pineapple.

Further, since the fumigation vaporizer is stable in structure and manipulation thereof is convenient, it is possible to minimize fumigant intake of workers, and thus to aim at the safe work.

While the present disclosure has been described with reference to the particular illustrative embodiments, it is not to be restricted by the embodiments but only by the appended claims. It is to be appreciated that those skilled in the art can change or modify the embodiments without departing from the scope and spirit of the present disclosure.

What is claimed is:

1. A fumigation vaporizer comprising:
   a housing including an inner cavity, and provided at an upper portion with an inlet port to supply a fumigant to the inner cavity and an outlet port to discharge a volatile fumigated substance from the inner cavity;
   a fumigant supply pipe configured to supply the fumigant to the inner cavity of the housing, one end of the fumigant supply pipe extending to the inner cavity through the inlet port, and the other end being connected to a fumigant reservoir;
   a heater configured to heat a lower portion of the housing, thereby producing the volatile fumigated substance by heating the fumigant supplied through the fumigant supply pipe;
   a non-explosive gas supply member provided to an outside of the housing to supply a non-explosive gas;
   a gas supply pipe having one end connected to the non-explosive gas supply member and the other end connected to the housing to supply the non-explosive gas to the inner cavity from the non-explosive gas supply member;
   a vessel-type heater installed to a portion of the gas supply pipe to heat the non-explosive gas supplied to the housing;
   a gas discharge pipe provided with a plurality of nozzle holes to spray the non-explosive gas supplied from a non-explosive gas tank, thereby supplying the non-explosive gas which is heated by the vessel-type heater to a lower portion of the housing, thereby upwardly moving the volatile fumigated substance; and
   a controller to control operation of the heater,
   the housing being provided with a heating hollow portion at the lower portion of the housing, in which the non-explosive gas heated and supplied by the vessel-type heater heats a bottom surface of the inner cavity while passing through the heating hollow portion, and
   a bottom surface of the heating hollow portion being provided with an inlet port through which the non-explosive gas passes, and a top surface of the heating hollow portion opposite to the inlet port being provided with an outlet port through which the non-explosive gas passing the heating hollow portion is supplied to the gas discharge pipe installed to the inner cavity.

2. The fumigation vaporizer according to claim 1, wherein the gas discharge pipe is a coil-shaped gas discharge pipe which is installed in a shape of a coil to the lower portion of the inner cavity, and
   a guide protrusion protrudes upwardly from a center portion of the coil-shaped gas discharge pipe so that the fumigant does not collect around a center portion of the gas discharge pipe, if a level of the fumigant goes down due to the volatile fumigated substance to be produced from the fumigant supplied to the inner cavity.

3. The fumigation vaporizer according to claim 2, wherein the guide protrusion is formed in any one of a hemispherical shape and a conic shape which protrudes upwardly from the center portion of the coil-shaped gas discharge pipe.

4. The fumigation vaporizer according to claim 2, wherein the non-explosive gas supply member includes the non-explosive gas tank which is filled with the non-explosive gas therein.

5. A fumigation vaporizer comprising:
   a housing including an inner cavity, and provided at an upper portion with an inlet port to supply a fumigant to the inner cavity and an outlet port to discharge a volatile fumigated substance from the inner cavity;
   a fumigant supply pipe configured to supply the fumigant to the inner cavity of the housing, one end of the fumigant supply pipe extending to the inner cavity through the inlet port, and the other end being connected to a fumigant reservoir;
   a heater configured to heat a lower portion of the housing, thereby producing the volatile fumigated substance by heating the fumigant supplied through the fumigant supply pipe;
   a non-explosive gas supply member provided to an outside of the housing to supply a non-explosive gas;
   a gas supply pipe having one end connected to the non-explosive gas supply member and the other end connected to the housing to supply the non-explosive gas to the inner cavity from the non-explosive gas supply member;
   a vessel-type heater installed to a portion of the gas supply pipe to heat the non-explosive gas supplied to the housing;
   a gas discharge pipe provided with a plurality of nozzle holes to spray the non-explosive gas supplied from a non-explosive gas tank, thereby supplying the non-explosive gas which is heated by the vessel-type heater to a lower portion of the housing, thereby upwardly moving the volatile fumigated substance; and
   a controller to control operation of the heater,
   the housing being provided with a heating hollow portion at the lower portion of the housing, in which the non-explosive gas heated and supplied by the vessel-type heater heats a bottom surface of the inner cavity while passing through the heating hollow portion, and a bottom surface of the heating hollow portion being provided with an inlet port through which the non-explosive gas passes, and a top surface of the heating hollow portion opposite to the inlet port being provided with an outlet port through which the non-explosive gas passing the heating hollow portion is supplied to the gas discharge pipe installed to the inner cavity, wherein the non-explosive gas supply member includes a nitrogen generator to continuously generate and supply a nitrogen gas, the nitrogen generator has a compressor configured to pressurize air sucked from the atmosphere and then supply the pressurized air to the nitrogen generator;

a first nitrogen separating tank supplied by the pressurized air from the compressor to separate nitrogen;

a second nitrogen separating tank supplied by the pressurized air from the compressor to separate nitrogen;

an absorbent respectively disposed in the first nitrogen separating tank and the second nitrogen separating tank to absorb oxygen contained in the air;

a nitrogen reservoir alternatively supplied by the nitrogen from the first nitrogen separating tank and the second nitrogen separating tank, and supplying the nitrogen to the housing through the gas supply pipe; and a controller to control concentration of the oxygen supplied to the first nitrogen separating tank and the second nitrogen separating tank so that an oxygen level is maintained at a level of 100 ppm, and the controller has an automatic time switch to variably produce a yield of the nitrogen from the nitrogen generator depending upon amounts of nitrogen to be used by the housing, and the automatic time switch variably controls a supply time of the pressurized air to be selectively supplied to the first nitrogen separating tank and the second nitrogen separating tank to produce the nitrogen, while the concentration of oxygen to be respectively supplied to the first nitrogen separating tank and the second nitrogen separating tank is maintained at the level of 100 ppm.

6. The fumigation vaporizer according to claim 1, wherein the heater is installed outside the housing and encloses an outer peripheral surface of the housing which corresponds to the lower portion of the housing.

7. The fumigation vaporizer according to claim 1, wherein the plurality of nozzle holes has a decreased-diameter hole which is formed in such a way that a diameter is gradually decreased toward a spray direction of the non-explosive gas, an orifice extended hole which communicates with the decreased-diameter hole, and is formed by an extended portion of a minimal diameter of the decreased-diameter hole, and an increased-diameter hole which communicates with the orifice extended hole, of which a diameter is gradually increased toward the spraying direction of the non-explosive gas.

8. The fumigation vaporizer according to claim 1, wherein the vessel-type heater is provided with a hot wire to heat the non-explosive gas, and the hot wire is arranged in any one of a zigzag shape, a U-shape and a spiral shape to promote heating.

9. The fumigation vaporizer according to claim 1, wherein the non-explosive gas is any one selected from a group consisting of nitrogen (N2), carbon dioxide (CO2), and helium (He), the fumigant is any one selected from a group consisting of methyl bromide, ethyl formate, methyl formate, liquefied fumigation substance (e.g., MITC, AITC or monoterpenes) mixable with ethyl formate, methyl isothicyante (MITC), allyl isothiocyanate (AITC), aluminum phosphide, magnesium phosphide, phosphine, sulfuryl fluoride, methyl iodide, cyanogen, metam sodium, carbonyl sulfide, carbon tetrachloride, and dimethyl disulfide, the housing and the outlet port are provided with a pressure gauge, respectively, and the housing is provided with a level gauge at one side thereof.

10. The fumigation vaporizer according to claim 1, wherein the gas discharge pipe is provided within the inner cavity.

11. The fumigation vaporizer according to claim 10, wherein the gas discharge pipe and the heater are arranged at the same level relative to the housing.

12. The fumigation vaporizer according to claim 10, wherein the heating hollow portion is provided below the inner cavity.

13. The fumigation vaporizer according to claim 12, wherein the vessel-type heater is provided outside the housing.

* * * * *